(12) United States Patent
DeLuca

(10) Patent No.: US 6,528,542 B2
(45) Date of Patent: Mar. 4, 2003

(54) CALCIUM FORMATE FOR USE AS A DIETARY SUPPLEMENT

(75) Inventor: Hector F. DeLuca, Deerfield, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/961,729

(22) Filed: Sep. 24, 2001

(65) Prior Publication Data

US 2002/0035151 A1 Mar. 21, 2002

Related U.S. Application Data

(63) Continuation of application No. 09/746,250, filed on Dec. 21, 2000, which is a continuation-in-part of application No. 09/649,710, filed on Aug. 25, 2000, now abandoned, and a continuation-in-part of application No. 09/469,513, filed on Dec. 22, 1999, now Pat. No. 6,160,016.

(51) Int. Cl.$^7$ .............................................. A61K 31/19
(52) U.S. Cl. ...................................................... 514/557
(58) Field of Search ......................................... 514/557

(56) References Cited

U.S. PATENT DOCUMENTS

| | | | |
|---|---|---|---|
| 2,266,992 A | 12/1941 | Roblin, Jr. | 167/68 |
| 3,558,786 A | 1/1971 | Eriksson et al. | 424/317 |
| 4,220,661 A | 9/1980 | Huitson | 424/317 |
| 4,851,221 A | 7/1989 | Pak et al. | |
| 4,870,105 A | 9/1989 | Fordtran | |
| 4,970,079 A | 11/1990 | Hem et al. | |
| 5,393,535 A | 2/1995 | Kjems | 404/678 |
| 5,629,025 A | 5/1997 | Shockley et al. | 424/680 |
| 5,631,289 A | 5/1997 | Abele | |
| 5,637,312 A | 6/1997 | Tock et al. | 424/317 |
| 5,686,111 A | 11/1997 | Jalbert | 424/489 |
| 5,698,222 A | 12/1997 | Mazer et al. | 424/464 |
| 5,905,093 A | 5/1999 | Achkar | 514/784 |
| 5,945,144 A | * 8/1999 | Hahn et al. | 426/74 |
| 6,160,016 A | 12/2000 | DeLuca | 514/557 |

FOREIGN PATENT DOCUMENTS

| | | |
|---|---|---|
| EP | 0 260 390 A1 | 3/1988 |
| FR | 2.196.151 | 3/1974 |
| JP | 59154053 | 2/1986 |
| WO | WO 97/30601 | 8/1997 |

OTHER PUBLICATIONS

A. Ghazali, et al., "Management of Hyperphosphatemia in Patients with Renal Failure," Curr. Sci. pp. 566–579, 1993.

C. Xu, et al., "Effects of High Calcium Intake on Fat Digestion and Bile Acid Excretion in Feces of Veal Calves," J. Dairy Sci. 81:2173–2177, 1998.

E. A. Slatopolsky, et al., "RenaGel®, a nonabsorbed calcium– and aluminum–free phosphate binder, lowers serum phosphorus and parathyroid hormone," Kidney Internat. 55:299–307, 1999.

R. J. Cook, et al., "Methanol Toxicity and Formate Oxidation in NEUT2 Mice," Arch. Biochem. Biophys. 393(2):192–198, 2001.

P. Damian and O. G. Raabe, "Toxocokinetic Modeling of Dose–Dependent Formate Elimination in Rats: In Vivo–In Vitro Correlations Usign the Perfused Rat Liver," Toxicol. App. Pharm. 139:22–32. 1996.

J. T. Eells, et al., "Methanol Poisoning and Formate Oxidation in Nitrous Oxide–Treated Rats," J. Pharm. Exp. Therap. 217(1):57–61, 1981.

J. T. Eells, et al., "Formate–Induced Alterations in Retinal Function in Methanol–Intoxicated Rats," Toxic. App. Pharm. 140:58–69, 1996.

J. T. Eells, et al., "Development and Cahracterization of a Rodent Model of Methanol–Induced Retinal and Optic Nerve Toxicity," Neuro Toxicology 21(3):321–330, 2000.

D. A. Fox and W. K. Boyes, "Toxic Responses of the Ocual and Visual System," in Casarette & Doull's Toxicology, C. D. Klaassen, Ed., 6th Ed., McGraw–Hill, New York, pp. 565–594, 2001.

F. C. Johlin, et al., "Studies on the Role of Folic Acid and Folate–Dependent Enzymes in Human Methanol Poisoning," Molec. Pharm. 31:557–561, 1987.

J. Liesivuori and H. Savolainen, "Urinary Formic Acid as an Indicator of Occupational Exposure to Formic Acid and Methanol," Am. Ind. Hyg. Assoc. J. 48(1):32–34, 1987.

J. Liesivuori and H. Savolainen, "Methanol and Formic Acid Toxicity: Biochemical Mechanisms," Pharm. Toxicol. 69:157–163, 1991.

J. Liesivuori, et al., "Kinetics and Renal Effects of Formic Acid in Occupationally Exposed Farmers," Arch. Toxicol. 66:522–524, 1992.

A. B. Makar, et al., "Formate Metabolism in Young Swine," Toxicol. App. Pharm. 105:315–320, 1990.

G. Malorny, "Metabolic Testing with Sodium Formiate and Formic Acid [AS] in Humans," Zeitschrift fur Ernahrungswissenshaft 9(4):340–348, 1969. (German translation included).

M. K. Martinasevic, et al., "Folate and 10–Formyltetrahydrofolate Dehydrogenase in Human and Rat Retina: Relation to Methanol Toxicity," Toxicol. App. Pharm. 141:373–381, 1996.

K. E. McMartin, et al., "Methanol Poisoning. V. Role of Formate Metabolism in the Monkey," J. Pharm. Exp. Therap. 201(3):564–572, 1977.

A. Nihlen and P.–O. Droz, "Toxicokinetic Modelling of Methyl Formate Exposure and Implications for Biological Monitoring," Int. Arch. Occup. Environ. Health 73:479–487, 2000.

(List continued on next page.)

Primary Examiner—Theodore J. Criares
Assistant Examiner—Jennifer Kim
(74) Attorney, Agent, or Firm—Quarles & Brady LLP

(57) ABSTRACT

A calcium format composition for oral administration to an individual for the purpose of supplementary dietary calcium is disclosed.

9 Claims, No Drawings

OTHER PUBLICATIONS

J. D. Osterloh, et al., "Serum Formate Concentrations in Methanol Intoxication as a Criterion for Hemodialysis," Annals Intern. Med. 104:200–203, 1986.

J. D. Osterloh, et al., "Serum Concentrations of Methanol After Inhalation at 200 ppm," JOEM 38(6):571–576, 1996.

M. T. Seme, et al., "Formate–Induced Inhibition of Photoreceptor Function in Methanol Intoxication," J. Pharm. Exp. Therap. 289(1):361–370, 1999.

T. R. Tephly, "The Toxicity of Methanol," Life Sciences 48:1031–1041, 1991.

J. Timbrell, "Principles of Biochemical Toxicology," 3rd Ed., Taylor & Francis, London, pp. 330–334, 2000.

R. P. Heaney, et al., "Calcium Abosorbability from Spinach," Am. J. Clinc. Nutr. 47:707–709, 1988.

D. M. Hegsted, "Major Minerals," Modern Nutrition in health and Disease, pp. 268–286, 1973.

J. D. Kopple, "Nutrition and the Kidney,"Human Nutrition, A Comprehensive Treatise, Nutrition, Metabolic and Clinical Applications, Plenum Press, New York and London, pp. 409–457, 1979.

* cited by examiner

CALCIUM FORMATE FOR USE AS A DIETARY SUPPLEMENT

CROSS-REFERENCE TO RELATED APPLICATION

This application is a continuation of U.S. Ser. No. 09/746,250, filed Dec. 21, 2000 which is a continuation-in-part of U.S. Ser. No. 09/469,513, filed Dec. 22, 1999 now U.S. Pat. No. 6,160,016 and 09/649,710, filed Aug. 25, 2000 now abandoned. All of these documents are incorporated by reference as if set forth fully herein.

STATEMENT REGARDING FEDERALLY SPONSORED RESEARCH OR DEVELOPMENT

BACKGROUND OF THE INVENTION

A. Calcium Format as a Phosphate Binder

Phosphorus retention plays a major role in chronic renal failure in the development of both secondary hyperparathyroidism and osteodystrophy. Bricker, N., S. et al., *Archives of Internal Medicine* 123:543–553 (1969); Rubini, M. E. et al., *Archives of Internal Medicine* 124:663–669 (1969); Slatopolsky, E., et al., *Journal of Clinical Investigation* 50:492–499 (1971); Bricker, N. S., *New England Journal of Medicine* 286:1093–1099 (1972); Slatopolsky, E. S., et al., *Kidney Int.* 2:147–151 (1972).

Antacids are often used to bind dietary phosphorus to prevent phosphorus retention and prevent its absorption. This process is referred to as phosphorus binding and appears to be a chemical reaction between dietary phosphorus and the cation present in the binder compound, which is usually albumin or calcium. The binding results in the formation of insoluble and unabsorbable phosphate compounds, adsorption of phosphorus ions on the surface of binder particles, or a combination of both.

Presently-used antacids are inefficient at binding phosphorus in vivo. For example, a recent study by Ramirez, et al., noted that even though aluminum-containing or calcium-containing antacids were administered in large excess, they bound only 19–35 percent of dietary phosphorus. Ramirez, J. A., et al., *Kidney Int.* 30:753–759 (1986). Similar conclusions can be derived from data presented in earlier studies. Kirsner, J. B., *Journal of Clinical Investigation*, 22:47–52 (1943); Clarkson, E. M., et al., *Clinical Science* 43:519–531 (1972); Cam, J. M., et al., *Clinical Science and Molecular Medicine* 51:407–414 (1976); Man, N. K. et al., *Proceedings of the European Dialysis and Transplantation Association* 12:245–55 (1975).

Antacids are used widely, often in large quantities, for indigestion, heartburn or peptic ulcer disease. Despite their consumption in large amounts and often over long periods of time, phosphorus depletion is uncommon in these settings. This fact is additional evidence of the inefficiency of antacids as phosphorus binding agents.

The inefficiency of commonly used phosphorus binders creates a clinical dilemma. The dose of the binder must be increased to control hyperphosphatemia, but increased risk of toxicity of the binder results from the increased dose. This toxicity includes bone disease and aluminum dementia from aluminum-containing antacids and hypercalcemia and soft tissue calcification from calcium-containing antacids. These risks are particularly problematic in patients with chronic renal disease.

It would be very useful to have a phosphorus binder available which does not have the risks associated with ingestion of presently available binders. The binder should be more efficient in binding phosphorus and, thus, would not have to be consumed in the large quantities necessary, for example, when calcium carbonate-containing compositions are used. Such a phosphorus binder would be particularly valuable for administration to individuals with chronic renal failure, in whom phosphorus retention is a serious concern and the risk of toxicity from consumption of presently available binders is greater than in individuals in whom kidney function is normal.

U.S. Pat. No. 4,870,105 addresses these concerns by disclosing a calcium acetate phosphorus binder. However, it would be advantageous to find a binder with a smaller anion and, hence, a smaller effective dose.

B. Calcium Format as a Dietary Supplement

Calcium is an abundant element in the human body and plays an important role in many physiological processes. Nutritional and metabolic deficiencies of calcium can have adverse effects, typically manifested through deficiencies in the structure, function and integrity of the skeletal system. The most common calcium-modulated metabolic bone disorder is osteoporosis.

A preferred approach to calcium supplementation is through dietary sources. Dairy products are the major contributors of dietary calcium, as are green vegetables (e.g. broccoli, kale, turnip greens, Chinese cabbage), calcium-set tofu, some legumes, canned fish, seeds and nuts. Breads and cereals can contribute significantly to calcium intake.

Calcium supplements may be the preferred way to obtain supplemental calcium. Calcium carbonate is usually recommended for economic reasons. However, calcium carbonate usage requires sufficient gastric acids for its utilization. Some individuals, especially the elderly, may have limited amounts of gastric acid, and achlorhydric patients have little gastric acid. For such cases, calcium carbonate is poorly utilized. Using large amounts of calcium carbonate may also lead to constipation and abdominal distention. Calcium lactate or calcium citrate may then be used.

Needed in the art of calcium supplementation is a very soluble calcium supplement with smaller anion and, hence, a smaller effective dose.

SUMMARY OF THE INVENTION

In one embodiment, the present invention relates to a method of binding phosphorus in the gastrointestinal tract and, thus, reducing phosphorus absorption from the intestine. It also relates to a method of reducing serum phosphate levels because phosphorus bound in the gastrointestinal tract results in lower phosphorus absorption than would otherwise occur. It is particularly useful in the treatment and prevention of hyperphosphatemia in individuals with renal disease or other disease in which the ability to excrete phosphorus from the body (e.g., in the urine) is impaired.

The method of the present invention comprises orally administering to an individual a composition which includes calcium format in sufficient quantity to effectively bind phosphorus, preferably present in food and beverages consumed by the individual, and prevent its absorption in the intestine. In an advantageous form of the invention, the calcium format is administered at a dose of between 0.5 and 10.0 grams.

The present invention is also a method of using calcium format as a dietary calcium supplement. The method comprises orally administrating to an individual a composition comprising calcium format in sufficient quantities to improve calcium balance or retention.

In an advantageous form of the invention, the calcium format is administered in a dose between 0.5 and 3.0 g/day as a supplement.

The present invention is also a pharmaceutical composition comprising calcium format in combination with a pharmaceutically acceptable carrier. In a preferred embodiment, the composition comprises 0.5 grams of calcium format per capsule or tablet. In another preferred embodiment, the composition comprises calcium format and at least one additional therapeutic ingredient. In a most preferred embodiment, this therapeutic ingredient is a vitamin D compound, typically cholecalciferol.

It is a feature of the present invention that the amount of calcium containing compound sufficient to inhibit gastrointestinal phosphorus absorption is 10% lighter than therapeutically equivalent amounts of previously known calcium acetate compounds.

It is another feature of the present invention that calcium format may be supplied orally to an individual in order to supplement the individual's calcium intake.

Other objects, features and advantages of the present invention will become apparent to one of skill in the art after review of the specification and claims.

DETAILED DESCRIPTION OF THE INVENTION

The present invention relates to a calcium format composition for oral administration to an individual. The composition is useful in reducing phosphorus absorption in the gastrointestinal tract. Calcium format is shown below to be effective in inhibiting phosphorus absorption when administered orally in in vivo tests and has been shown to prevent the absorption of ingested phosphorus at a lower dose than other calcium-containing binders. As a result of these discoveries, calcium format, alone or in combination with other materials, can be used to bind phosphorus in the gastrointestinal tract, thus reducing the percentage of an amount of phosphorus consumed (i.e., of a given "dose" of phosphorus) which is absorbed. Preferably, this dose would be 0.5–10.0 grams when adjusted to doses intended for human patients.

The present invention also relates to a method of inhibiting gastrointestinal phosphorus absorption. The method of the present invention is based on the demonstration that calcium format is an effective binder of phosphorus when administered orally to an individual. The method comprises orally administering a quantity of calcium format sufficient to bind with phosphorus in the gastrointestinal tract. Preferably, this dose is between 10–200 milliequivalents of calcium and is preferably present in either tablet or gelatin capsule form. In a most preferable form of the present invention, the oral dose is ingested at mealtimes.

As a result of the present invention it is possible to administer calcium format to reduce absorption of dietary phosphorus, which has the net effect of reducing the risks of adverse effects (e.g., bone disease and secondary hyperparathyroidism) observed in individuals (e.g., chronic renal patients) in whom the ability to excrete phosphorus in the urine is impaired.

As used herein, the term "phosphorus" includes phosphorus and phosphate in its various forms (e.g. $HPO_4^-$, $PO_4^{-3}$, etc.).

According to the method of the present invention, calcium format is administered, alone or in combination with other substances (e.g., in a hard gelatin capsule; along with materials necessary to form a tablet or caplet as a delivery vehicle for the calcium format; or along with a second phosphorus binder or other pharmaceutically useful substance) in sufficient quantities to reduce phosphorus absorption in the gastrointestinal tract. The calcium format is administered orally, preferably close in time to food and beverage consumption. By "at mealtimes" we mean within 30 minutes of a meal.

In one embodiment, 0.5–10.0 grams of anhydrous calcium format (10–200 milliequivalents calcium) is taken prior to food consumption (e.g., meal time) and a second dose of 0.5–10.0 grams of anhydrous calcium format is taken after food consumption. The dose or quantity to be taken at a given time varies on an individual-by-individual basis and can be adjusted as needed (e.g., by monitoring serum concentration of phosphorus and calcium).

In another embodiment of the present invention, calcium format is administered, alone or in combination with other substances, in sufficient quantities to supplement an individual's calcium intake. The Examples below indicate that calcium format in quantities between 0.5 and 3.0 g/day are sufficient to improve calcium balance, bone density and calcium retention.

The present invention is also a pharmaceutical composition comprising calcium format in a pharmaceutically acceptable carrier, wherein the calcium format is present in an amount between 0.5–1.0 grams. In another embodiment, the pharmaceutical composition comprises calcium format in amount suitable to inhibit gastrointestinal absorption of phosphorus, provides between 11 and 44 milliequivalents of calcium, and is 10% lighter than the corresponding calcium acetate dose and is the richest form of calcium available. By "corresponding" or "therapeutically equivalent," we mean a dose that is equally effective.

In another embodiment of the present invention, the pharmaceutical composition essentially comprises only calcium format and at least one pharmaceutically carrier, wherein the calcium format is present in an amount sufficient to produce between 11 and 44 milliequivalents of calcium. By "essentially comprises" we mean that calcium format is the only active ingredient in the pharmaceutical composition.

The present invention is also a pharmaceutical composition comprising calcium format in a pharmaceutically acceptable carrier combined with other therapeutic agents, preferably a vitamin D compound. Most preferably, the calcium format is combined with vitamin D is cholecalciferol in a range of 125 IU to 400 IU in a tablet or capsule.

EXAMPLE 1

Calcium Format as a Phosphate Binder in Normal Rats

TABLE 1

| Group | % Ca Formate | Serum (mg %) (mean ± SEM) | Weight | Serum Ca (mg %) (mean ± SEM) |
|---|---|---|---|---|
| 1 Week on Diet ||||| 
| 1 | 0 | 4.96 ± .48 | 209 ± 5.5 | ND |
| 2 | 1 | 3.25 ± .31 | 229 ± 5.5 | ND |
| 3 | 2 | 2.50 ± .32 | 211 ± 6.3 | ND |
| 4 | 3 | 2.5 ± .20 | 194 ± 6.5 | ND |

TABLE 1-continued

| Group | % Ca Formate | Serum (mg %) (mean ± SEM) | Weight | Serum Ca (mg %) (mean ± SEM) |
|---|---|---|---|---|
| 2 Weeks on Diet | | | | |
| 1 | 0 | 5.98 ± .39 | 295 ± 4.8 | 11.4 ± .20 |
| 2 | 1 | 4.70 ± .62 | 211 ± 3.8 | 14.0 ± .51 |
| 3 | 2 | 2.7 ± .24 | 198 ± 5.2 | 12.8 ± .94 |
| 4 | 3 | 2.9 ± 0.8 | 150 ± 8.0 | 12.9 ± 1.3 |

ND = not determined. There were at least 6 rats per group.

Five-week-old Sprague Dawley rats were given a synthetic diet containing 0.47% Ca and 0.2% phosphorus for two weeks prior to the addition of calcium format to the diet. Body weights were measured and blood serum was collected after one or two weeks on calcium format.

The results of this experiment are tabulated in Table 1. All rats supplied with calcium format had less serum phosphorus than control rats. There seemed to be little difference in serum phosphorus between rats on 2% or 3% calcium format, thus indicating that a saturation binding point had been reached.

EXAMPLE 2

Twenty 15-day-old weanling rats from Holzmann Company were placed on a an adequate synthetic diet called "Diet 11" (Suda, T., et al., *J. Nutr.* 100:1049–1052, 1970). This diet is supplemented with vitamins A, D, E and K as described in that paper. Therefore, these are vitamin D-sufficient animals.

The animals were then placed on a basal diet that contains 0.02% calcium, i.e. an extremely low calcium diet. These animals served as controls. Another group were placed on the same diet containing calcium format, providing calcium at 0.25% of the diet. Another group was supplied calcium format at 0.47% calcium in the diet, and another group was provided 0.47% calcium in the form of calcium carbonate. Growth of the animals reflects the ability of the animals to utilize calcium. Using a growth assay of this type to illustrate the effectiveness of the calcium salt is supported by Steenbock, H. and D. C. Herting, *J. Nutr.* 57:449–468,1955.

Table 2, below, tabulates the results. Referring to Table 2, we conclude that calcium format is at least equal to calcium carbonate in ability to supply calcium to experimental rats. In fact, there is a slightly better growth obtain with 0.25% calcium as the format in comparison to other treatment groups. Calcium format can therefore be used as a dietary supplement to provide dietary calcium.

TABLE 2

| | Average Body Weight in Grams ± S.E.M for 5 Rats | | | |
|---|---|---|---|---|
| | Control Diet | Calcium Formate | | Calcium Carbonate |
| Day | (0.02% Ca) | (0.25% Ca) | (0.47% Ca) | (0.47% Ca) |
| 7 | 47.6 ± 10.8 | 54.3 ± 4.0 | 51.0 ± 10.6 | 48.6 ± 4.9 |
| 14 | 74 ± 10.7 | 84.6 ± 5.5 | 78.0 ± 19 | 80.4 ± 10.4 |
| 21 | 85.6 ± 10 | 131.0 ± 5.7* | 127 ± 11* | 126.2 ± 11* |

*Significantly different from control by Students 't' test. P < 0.001.

I claim:

1. A method of increasing dietary calcium in a human patient, comprising:

orally ingesting a quantity of between 0.5 and 3.0 g per day of calcium format, wherein the quantity is sufficient to improve calcium balance or retention.

2. The method according to claim 1 wherein the calcium format is in tablet form.

3. The method according to claim 1 wherein the calcium format is in gelatin capsule form.

4. The method of claim 1 wherein the calcium format is orally ingested in a first and second dose, wherein the first dose is before a mealtime and the second dose is after a mealtime.

5. The method of claim 1 wherein the quantity is administered once a day.

6. The method of claim 1 wherein the calcium format is combined in a dose with a second, biologically active compound.

7. A The method of claim 6 wherein the second compound is a vitamin D compound.

8. The method of claim 7 wherein the vitamin D is cholecalciferol.

9. The method of claim 8 wherein the cholecalciferol is between 125 IU and 400 IU.

* * * * *

UNITED STATES PATENT AND TRADEMARK OFFICE
CERTIFICATE OF CORRECTION

PATENT NO. : 6,528,542 B2
DATED : March 4, 2003
INVENTOR(S) : Hector F. DeLuca

It is certified that error appears in the above-identified patent and that said Letters Patent is hereby corrected as shown below:

Column 1,
Line 18, "calcium format" should read -- calcium formate --.

Column 2,
Lines 15, 57, 61, 64 and 66, "calcium format" should read -- calcium formate --.

Column 3,
Lines 2, 5, 8, 9, 19, 28, 31, 36, 46, 48, 55 and 56, "calcium format" should read -- calcium formate --.

Column 4,
Lines 2, 5, 11, 13, 19, 22, 27, 28, 30, 39, 40, 42, 47, 50 and 55, "calcium format" should read -- calcium formate --.

Column 5,
Lines 16, 18, 20, 23, 37, 39 and 46, "calcium format" should read -- calcium formate --.
Line 28, "a an adequate" should read -- an adequate --.

Column 6,
Lines 4, 27, 29, and 35, "calcium format" should read -- calcium formate --.
Line 30, "a an adequate" should read -- an adequate --.

Signed and Sealed this

Seventh Day of October, 2003

JAMES E. ROGAN
*Director of the United States Patent and Trademark Office*